United States Patent
Watanabe et al.

[11] Patent Number: 5,843,784
[45] Date of Patent: Dec. 1, 1998

[54] RADIO-DETECTION METHOD OF OXYGENATION REACTION

[75] Inventors: Yasuyoshi Watanabe, Minoh, Japan; Bengt Långström, Upsala, Sweden

[73] Assignee: Research Development Corporation of Japan, Japan

[21] Appl. No.: 713,479

[22] Filed: Sep. 13, 1996

[51] Int. Cl.[6] .............................. G01N 23/00; C12Q 1/28; C12Q 1/30

[52] U.S. Cl. .................................. 436/58; 435/4; 435/27; 435/28; 436/57; 436/127; 436/136

[58] Field of Search ................................ 436/58, 57, 127, 436/136; 435/4, 27, 28

[56] References Cited

PUBLICATIONS

M.M. Ter–Pogossian et al. *J. Clin. Invest*, 1970, 49, 381–391.
R.P. Fogel et al. *Nucl. Phys. A* 1972, 187, 624–636.
R.E. Bigler et al. *J. Nucl. Med.* 1981, 22, 959–965.
M. Yuasa et al. *Chem. Lett.* 1984, 1889–1892.
M. Sajjad et al. *Radiochim. Acta.* 1985, 38, 57–63.
M.M. Ter–Pogossian et al. *Semin. Nucl. Med.* 1985, 15, 377–394.
E. Meyer et al. *J. Cereb. Blood Flow Metab.* 1987, 7, 403–414.
B. Langstrom *Acta Radiol. Supp.* 1990, 374, 47–51.
M.S. Berridge et al *J. Nucl. Med.* 1990, 31, 1727–1731.
K.A. Vonkeman et al. *Stud. Surf. Gci Catal.* 1991, 71, 239–252.
G. Jonkers et al. *Nature* 1992, 355, 63–66.
B. Långström et al. *Dev. Nucl. Med.* 1995, 26, 37–50.
B. Hyllbrant et al. *J. Labelled Comp. Radiopharm.* 1995, 317, 704–705.
Y. Watanabe et al. *Biochem. Biophys. Res. Commun.* 1997, 231, 131–134.
Abstract of "The 68th Japan Biochemical Society Conference", Sep. 15 —Sep. 18, 1995.

*Primary Examiner*—Arlen Soderquist
*Attorney, Agent, or Firm*—Wenderoth, Lind & Ponack

[57] ABSTRACT

To permit detection of trace unstable reaction products to clarify the reaction process of oxygenation, this invenion provides a method of introducing positron nuclide $^{15}O$ as an oxygen additive into the reaction system.

5 Claims, 3 Drawing Sheets

RADIO-DETECTION METHOD OF OXYGENATION REACTION

FIELD OF THE INVENTION

The present invention relates to a radio-detection method of oxygenation. More particularly, the present invention relates to a novel radio-detection method which permits easier detection of trace metabolites even in a crude substance system, and allows clarification of mechanism of the oxygenation, oxidation and biochemical applications.

PRIOR ART AND PROBLEMS

Oxygen is an essential molecule for life. Recently, the general attention is attracted by many biochemical changes brought about by the result of oxidation stress as one of senescence mechanisms, and participation of oxygen in biomolecules is becoming an important problem. When considering metabolism as viewed from the point of view of oxygen, there have often been referred to the facts that cellular respiration produces energy (ATP), that it is important for biosynthesis of many physiologically active substances such as steroids, prostaglandin, catecholamine and serotonin by the action of a enzymatic oxygenation, and radicals produced from oxygen. There as however almost unavailable a report viewing these metabolites from oxygen molecule itself. This is attributable to the absence of a radioisotope easy to use for oxygen, as described later.

While enzyme plays an important role in biochemical reactions, on the other hand, it is not so easy to analyze its process of reaction. For example, the oxygenation is known as a reaction caused by enzyme, and the process of reaction is attracting researchers' interest as a reaction using oxygen in cells and bio-tissues. Actually, however, almost no means of its analysis has as yet been practicable. This is due to the fact that detection of trace unstable metabolites occurring in the course of reaction is very difficult.

The reaction process of the enzymatic oxygenation has of course been studied. For example, there is available a method using stable isotopes $^{18}O$ and $^{17}O$ to evidence the enzymatic oxygenation (for example, O. Hayaishi, 1957).

However, the methods using stable isotopes $^{18}O$ or $^{17}O$ popularly known to date is well applicable to a purified enzyme, but is hardly applicable to a complicated system such as cells or tissues. That is, it is impossible to detect a trace unstable substances in a more complicated system. A method for utilizing a radioisotope easy to use for oxygen atoms has not been invented.

These circumstances are not limited to enzymatic reactions: when, in a reaction such as a biosynthesis involving oxygen or a general chemical synthesis, a metal, or a complex or an oxide thereof is used as a catalyst, it is difficult to clarify the reaction mechanism, thus largely restricting progress of reaction technology.

The present invention has therefore an object to provide a novel method for detecting an oxygenation, which overcomes the restrictions in the conventional technology as described above, and permits detection, even in a more complicated system, of trace unstable substance in an enzymatic reaction and a trace intermediate compound in a catalytic reaction.

SUMMARY OF THE INVENTION

As means to solve the foregoing problems, the present invention provides a radio-detection method of oxygenation, which comprises the step of, in an oxygenation, introducing positron nuclide $^{15}O$ as an additive oxygen.

The present invention provides also embodiments of the foregoing method, in which stable isotopes $^{17}O$ and/or $^{18}O$ are simultaneously used, and in which $^{15}O$ prepared through the nuclear reaction, e.g., $^{14}N(d,n)^{15}O$ reaction is introduced by means of an oxygen-nitrogen mixed gas.

DETAILED DESCRIPTION OF THE INVENTION

The present invention makes it possible to, in oxygenation involving various substances, detect trace unstable metabolites or reaction intermediates which has conventionally been difficult to detect. It is thus possible to apply the present invention to clarification of reaction mechanism, studies on functions displayed in biological cells and tissues, and to various medical and biochemical uses as well as to chemical synthesis.

While $^{15}O$ has a relatively short physical half-life of 2.07 minutes, the specific radioactivity is high (theoretically $3.36 \times 10^{21}$ Bq/mol), so that it is very advantageous for search to trace unstable metabolites.

The label by $^{15}O$ is positron nuclide: for example, the one used for positron emission tomography is applicable, which may be introduced during oxygenation reaction.

There is no particular limitation on reaction substrate in enzymatic reaction, kind of enzyme, kind of raw material substance and catalyst in catalytic reaction and means for identifying the product, and various embodiments are possible.

When a stable isotope $^{17}O$ or $^{18}O$ is used simultaneously with $^{15}O$, i.e., when the double labelling method is complied with, the present invention provides an advantage of monitoring the presence of an unknown metabolite (oxygen additive) with $^{15}O$ and determining the structure of that portion from the presence of $^{17}O$ or $^{18}O$ without hurry, spending a sufficient time. Various embodiments are possible also for this simultaneous use.

Now, the present invention will be described further in detail by means of an example.

EXAMPLE

As a model of enzymatic oxygenation,

Substrate: Pyrocatechol

Enzyme: Metapyrocatechase were employed.

Figure 1:
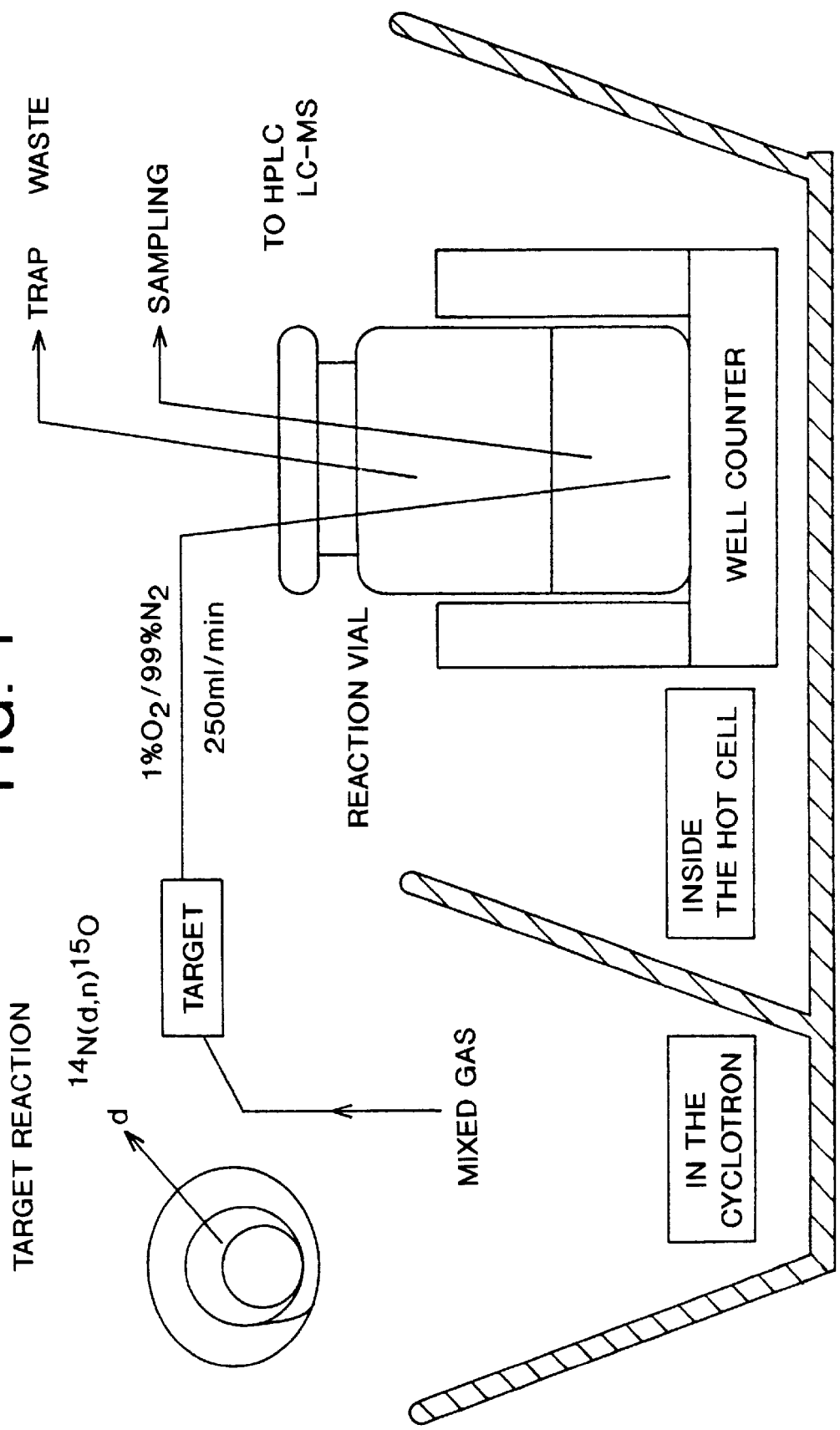
FIG. 1 shows a configurational diagram illustrating an experimental system.

FIG. 1 illustrates a typical experimental system for the model reaction in the present invention. $^{15}O$ was prepared through a steady $^{14}N(d,n)^{15}O$ reaction by means of a baby cyclotron, and was supplied to the experiment on an oxygen-nitrogen mixed gas flow at a ratio of 1% $O_2$/99% $N_2$ and a flow rate of 250 ml/min.

In this reaction, the substrate catechol was confirmed to have been converted into a single product having a radioactivity with time as expressed in the following formula:

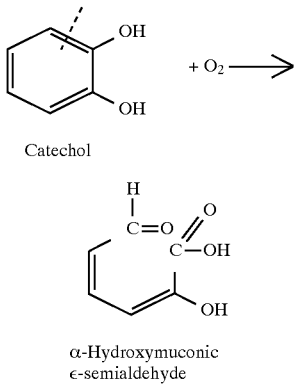

Catechol

α-Hydroxymuconic
ε-semialdehyde

The product was identified by means of HPLC and LC-MS.

Figure 2:
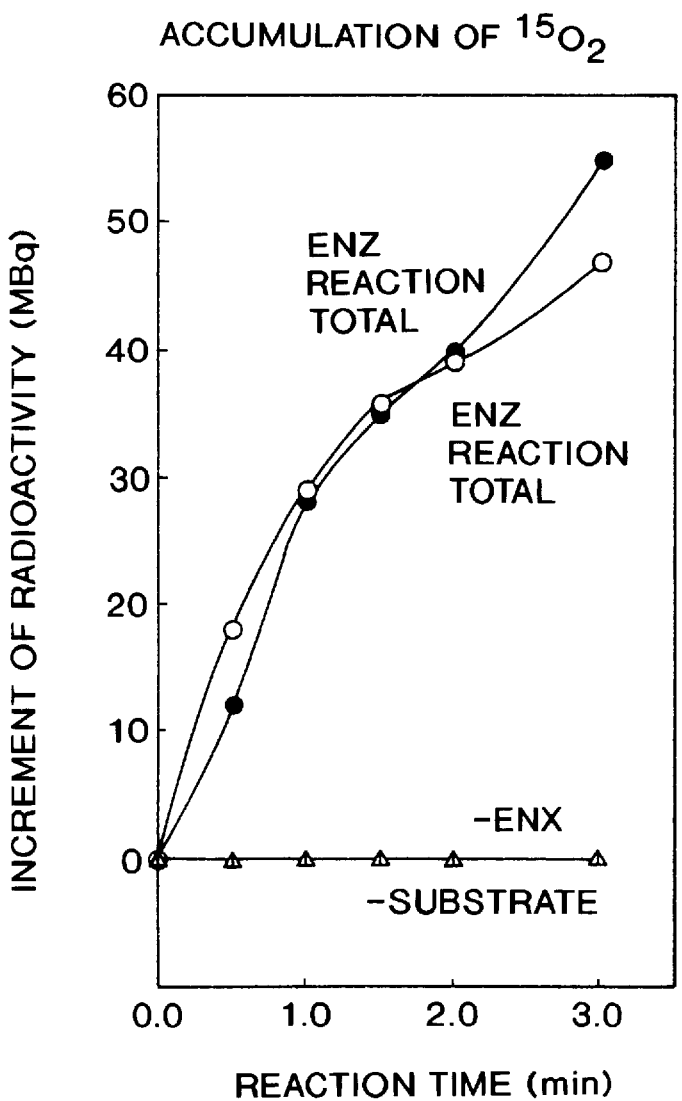
FIG. 2 shows a graph illustrating the relationship between the reaction time in an example and the detection radioactivity and FIG. 3 shows radio-UV-LC-MS spectral diagrams.
Figure 3A:
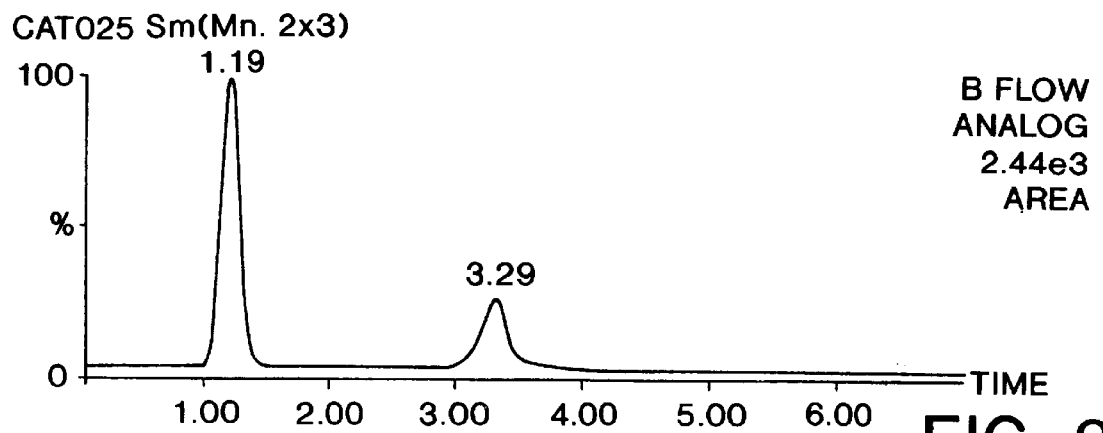
Figure 3B:
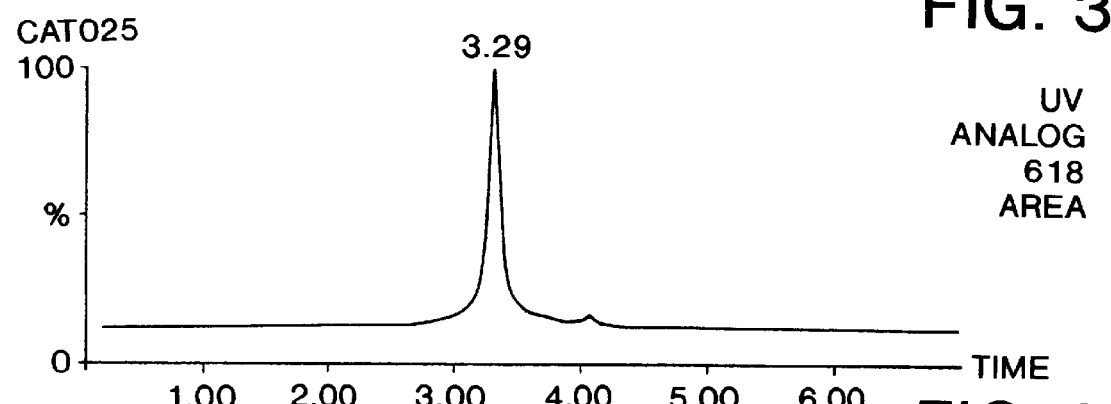
Figure 3C:
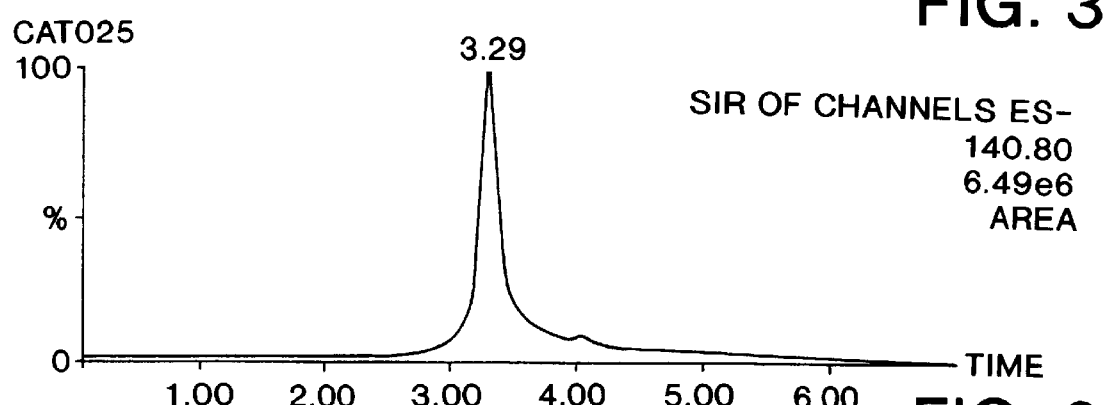
Figure 3D:
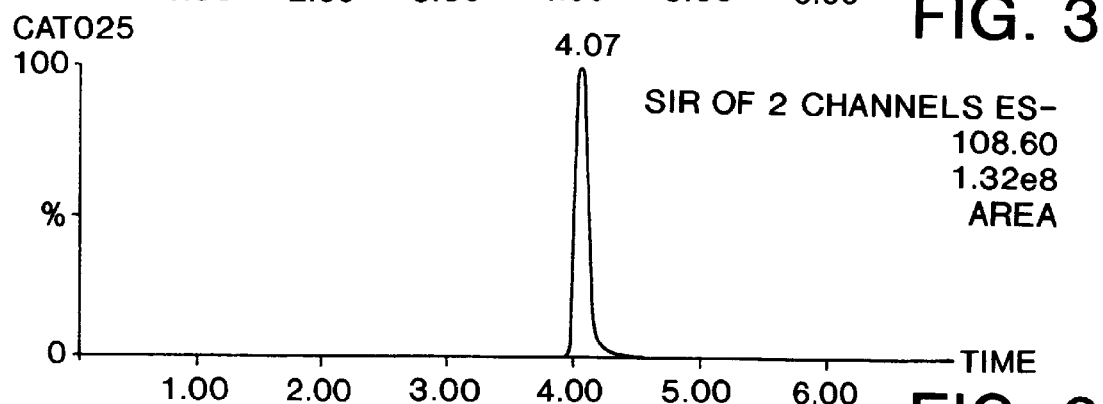

FIG. 2 illustrates the relationship between the reaction time having demonstrated the participation in the $^{15}O_2$ reaction and radioactivity. FIG. 3 shows the results of HPLC-mass spectrometry identification. Conditions for HPLC identification were as follows:

TABLE 1

| | | | |
|---|---|---|---|
| Volume: | 10 μl | | |
| Column: | KromaSil C18, 5μ | | |
| Size(mm): | 100 × 4.6 | | |
| λ: | 360 nm | | |
| Mobile phase A: | Aq | | |
| Mobile phase B: | $CH_3CN$ | | |
| Mobile phase C: | $CH_3CN$/Aq 50/50, 100 mM HOMe | | |
| Flow (ml/min): | 1 | | |
| Program: | Time | % B | % C |
| | 0 | 1 | 3 |
| | 0.1 | 1 | 3 |
| | 6.1 | 97 | 3 |
| | 7 | 97 | 3 |
| | 8 | 1 | 3 |
| | 10 | 1 | 3 |

FIG. 3 illustrates radio-UV-LC-MS spectra: the lowermost stage represents the substrate catechol. The first radioactive peak in the uppermost stage indicates $^{15}O$ in combination with the enzyme. Spectra for catechol and the products were scanned with 50 to 1,000 Da. Conditions for LC-MS identification were as follows:

TABLE 2

| | |
|---|---|
| Sm(Mn, 2 × 3) | Sm Smooth |
| | Mn Mean(smooth function) |
| | Window size (scans) +/−3 |
| | Number of smoothes 2 |
| ES− | Ionization mode: Negative electrospray |

TABLE 2-continued

| | |
|---|---|
| SIR | Selected Ion Recording |
| 31 (1.110) Cm (31:34 − (36:55 + 23:30) | written on spectra |
| | Spectra chosen at time 1.110 |
| | Cm Combine spectra |
| | This means that spectra 31:35 are combined under the chromatografic peak, spectra 36:55 and 23:30 are subtracted as background. |

$^{15}O$ was confirmed to be at a site as expressed in the following formula:

It is needless to mention that the present invention is not limited in any manner by the example presented above. Labelling with $^{15}O$ is possible in various reactions.

According to the present invention, as described above in detail, it is possible, as to a chemical reaction such as an enzymatic reaction involving oxygen or a catalytic reaction, to evaluate oxygenation activity, to detect a trace unstable substance such as an intermediate or the product of the reaction, to clarify the reaction mechanism, and furthermore, through simultaneous use of study with a stable isotope such as $^{18}O$ or $^{17}O$, to apply in areas of synthesis chemistry, biochemistry regarding the process of metabolism in cells and labelling, and in medical science.

What is claimed is:

1. In a method of detecting reaction products in an enzymatic oxygenation reaction system, the improvement which comprises introducing positron nuclide $^{15}O$ as an additive oxygen to the enzymatic reaction system and detecting radioactive products produced during the oxygenation reaction by use of radio-UV-LC-MS (liquid chromatography mass spectrometry with radio absorption detection).

2. The method of claim 1, wherein stable isotopes $^{17}O$ and/or $^{18}O$ are simultaneously introduced with $^{15}O$ into the oxygenation system.

3. The method of claim 1, wherein $^{15}O$ prepared through a $^{14}N(d,n)$ $^{15}O$ reaction is introduced into the oxygenation reaction system by means of an oxygen-nitrogen mixed gas.

4. The method of claim 2, wherein $^{15}O$ prepared through a $^{14}N(d,n)$ $^{15}O$ reaction is introduced into the oxygenation reaction system by means of an oxygen-nitrogen mixed gas.

5. The method of claim 1, wherein the radioactive products include trace metabolites.

* * * * *

UNITED STATES PATENT AND TRADEMARK OFFICE
CERTIFICATE OF CORRECTION

PATENT NO. : 5,843,784
DATED : December 1, 1998
INVENTOR(S) : Yasuyoshi WATANABE et al.

It is certified that error appears in the above-identified patent and that said Letters Patent is hereby corrected as shown below:

On the title page,
                            insert the following:

--[30]  Foreign Application Priority Data
  March 18, 1996   [JP]  Japan . . . . . . . . . .  8-060680--.

Signed and Sealed this

First Day of June, 1999

Attest:

Attesting Officer

Q. TODD DICKINSON

Acting Commissioner of Patents and Trademarks